United States Patent [19]

Renirie et al.

[11] Patent Number: 5,369,364
[45] Date of Patent: Nov. 29, 1994

[54] BATTERY STATE OF CHARGE DETERMINATION WITH PLURAL PERIODIC MEASUREMENTS TO DETERMINE ITS INTERNAL IMPEDANCE AND GEOMETRIC CAPACITANCE

[75] Inventors: Wim C. M. Renirie, Berg en Dal, Netherlands; Craig L. Schmidt, Eagan, Minn.

[73] Assignee: Medtronic, Inc., Minneapolis, Minn.

[21] Appl. No.: 53,108

[22] Filed: Apr. 26, 1993

[51] Int. Cl.⁵ .......................................... G01N 27/416
[52] U.S. Cl. ................................. 324/430; 324/436; 340/636
[58] Field of Search .................. 320/48; 324/426, 429, 324/430, 436; 340/636; 128/696, 706

[56] References Cited

U.S. PATENT DOCUMENTS

| | | | |
|---|---|---|---|
| 3,562,634 | 2/1971 | Latner | 324/427 |
| 4,231,027 | 10/1980 | Mann et al. | 340/636 |
| 4,259,639 | 3/1981 | Renirie | 324/430 |
| 4,324,251 | 4/1982 | Mann | 128/419 PT |
| 4,678,998 | 7/1987 | Muramatsu | 324/427 |
| 4,743,855 | 5/1988 | Randin et al. | 324/430 |
| 5,137,020 | 8/1992 | Wayne et al. | 128/419 PS |
| 5,241,275 | 8/1993 | Fang | 324/430 |

OTHER PUBLICATIONS

E. Willihnganz et al, "Battery Impedance-Farads, Milliohms, Microhenries", Sep. 1959, pp. 922–925.

Primary Examiner—Kenneth A. Wieder
Assistant Examiner—Christopher M. Tobin
Attorney, Agent, or Firm—Harold R. Patton

[57] ABSTRACT

A method and apparatus for measuring the depletion level (depth of discharge) of a lithium-iodine battery in an implantable medical device. A first set of measurements are made to determine the internal impedance of the battery, and a second set of measurements are made to determine the geometric capacitance of the battery, which has been found to correlate closely to the depth of discharge of the battery. The measurements are all made while the pacemaker is first temporarily decoupled from the medical device circuitry. The first measurements are made during a time window following a known change in resistive load across the terminals of the battery, and are capable of being correlated with 1-kHz qualification testing data made on the battery at the time of manufacture. The second measurements are made when the known load is periodically coupled and decoupled to the terminals of the battery at a rate of 80-kHz. The resulting data can be used to monitor depth of discharge throughout the operable life of the battery.

4 Claims, 6 Drawing Sheets

BATTERY STATE OF CHARGE DETERMINATION WITH PLURAL PERIODIC MEASUREMENTS TO DETERMINE ITS INTERNAL IMPEDANCE AND GEOMETRIC CAPACITANCE

FIELD OF THE INVENTION

This invention relates to the field of implantable medical devices, and more particularly relates to circuits for determining the depth of discharge of lithium-iodine batteries in a pacemaker or other battery-powered medical device.

BACKGROUND OF THE INVENTION

The number of patients with implanted pacemakers, cardioverters, defibrillators, neural stimulators, and the like is steadily increasing around the world, and is likely to continue to do so. A great many of these patients are partially or completely dependent upon their implanted devices, and it is very important for implanted devices to operate reliably. It has always been desirable for a clinician to be able to readily obtain reliable information about various aspects of an implanted device's operational status. The status of the device's power supply is of particular concern.

The most prevalent source of power used in implanted devices is battery power, very often from lithium-iodine cells. Many systems have been proposed in the prior art for providing some sort of battery end-of-life (EOL) indication when the device's power supply is nearly depleted. Of course, it is desirable for the circuitry for generating the EOL indication to be able to anticipate battery depletion early enough to allow time for appropriate remedial action to be taken, such as replacement of the device.

With the advent of improved batteries which can last for many years before depletion, the need has arisen for more information than a simple EOL indication. For example, it has been deemed desirable for the device to provide information regarding how much longer the battery will last under the normal demand that is placed on it.

Lithium-iodine batteries have a characteristic feature that their internal resistance curve is substantially linear as a function of energy depletion until near EOL, at which time the curve exhibits a "knee" where internal resistance begins to rise rapidly. In lithium-iodine batteries, the cell cathode consists of molecular iodine weakly bonded to polyvinyl pyridine (P2VP). The initial cathode composition of lithium-iodine batteries is often expressed as the weight ratio of $I_2$ to P2VP. Typical values of this ratio range from 20:1 to 50:1. No electrolyte as such is included in the construction of the cell, but a lithium iodine (LiI) electrolyte layer forms during cell discharge, between the anode and the cathode. The LiI layer presents an effective internal resistance to Li+ ions which travel through Since the LiI layer grows with the charge drawn from the battery, this component of the battery resistance increases linearly as a function of energy depletion. In the implantable device context, where there is typically a relatively continuous energy depletion, this component of the internal resistance increases continually over time. However, particularly for a demand type pacemaker which at any given time may or may not be called upon to deliver stimulating pulses, the increase in this component is continuous but not necessarily linear with time, due to the fact that current drain is not constant.

Another component of internal resistance in lithium-iodine cells is caused by depletion of iodine in the cathodes. The cathode is essentially a charge transfer complex of iodine and P2VP, and during discharge of the cell iodine is extracted from this complex. As noted above, the weight ratio of $I_2$ to P2VP at beginning of life may range from 20:1 to 50:1. During extraction of iodine from the complex, the resistance to this process is low until the point is reached where the $I_2$-to-P2VP ratio is reduced to approximately 8:1, the ratio at which the cathode becomes a single phase and the iodine activity begins to be less than unity. At this point the resistance rises sharply. This gives rise to a non-linear internal resistance component which, for the lithium-iodine cell, is called variously the depletion resistance, depolarizer resistance, the charge-transfer complex resistance, or the pyridine resistance. By whatever names, the combination of the non-linear component with the linear component produces an overall resistance curve with a knee occurring toward EOL, the knee being caused by the reaching of the depletion of available charge carriers from the cathode.

In the prior art, some EOL indicator arrangements in implantable devices evaluate battery life based simply upon the terminal voltage of the battery, indicating EOL when the voltage falls below a predetermined threshold. However, due to the internal impedance of the battery, terminal voltage varies significantly depending upon current consumption. Thus, if relatively little current is drawn from the battery for a period of time when the battery is nearing but has not reached its EOL, a sudden prolonged period of high demand on the battery may cause a situation in which too little time is available between indication of EOL and total depletion of the battery. For a particular pacemaker and electrode combination in a given patient, there will be a variation in the effective load on the lithium-iodine battery, and a resulting variation in the overall current drain. Accordingly, if an EOL indication is predicated upon sensing the voltage of the battery and detecting when it drops below a certain level, there can be very little assurance that the level chosen will correspond to the knee of the internal resistance curve.

It has been recognized in the prior art that since remaining battery life is directly related to the internal impedance of the battery itself, remaining battery life can be reliably predicted through accurate measurement of internal battery impedance. In U.S. Pat. No. 5,137,020 issued to Wayne et al. and assigned to the assignee of the present invention, there is described a battery impedance measuring arrangement wherein a current source and a reference impedance are applied to a battery which has been isolated from the remainder of the pacemaker circuitry. The Wayne et al. '020 patent is hereby incorporated by reference in its entirety into the present disclosure.

Other battery impedance measuring arrangements are proposed, for example, in U.S. Pat. Nos. 4,259,639 (Renirie), 4,231,027 (Mann et al.) and 4,324,251 (Mann). These patents are also hereby incorporated by reference herein in their entirety. The theory underlying the use of internal impedance as a EOL warning indicator is that at low current drains typical of implantable medical devices, plots of resistance versus time give more warning than plots of terminal voltage over time. If voltage characteristics for different current drains are considered, the knees in the impedance curve are observed to have a fairly wide variation, meaning that the voltage at which the knee might appear is similarly subject to substantial variation as a function not only of the particular battery being used but also of the current being drawn by the pacemaker circuitry at a given time. On the other hand, plots of resistance indicate that the knee varies over a smaller range of values of internal resistance. Since the current drain may vary drastically with different electrode loads, the variation in voltage may be much greater than the variation in internal resistance. Monitoring the internal resistance thus provides a more direct indication of the depth of discharge of the battery, whereas monitoring the output voltage gives a much less direct indication, reflecting not only the depth of discharge but also the current drain.

Although internal impedance is an accurate and reliable indicator that a battery is nearing EOL than battery terminal voltage, the nature of the internal impedance curve is such that it provides the most information relatively near EOL, and conveys less information about battery condition in the early and middle stages of discharge. As previously noted, the increasing life expectancies of state-of-the-art implantable devices makes it ever more important to be able to monitor the condition of batteries throughout their life.

In accordance with one aspect of the present invention, therefore, there is provided a means for more accurately measuring the internal impedance of a lithium-iodine battery. In accordance with another aspect of the present invention, there is also provided a means for obtaining information about battery depletion during early and middle stages of discharge, so that a battery monitoring circuit can reliably indicate more than the imminent exhaustion of the battery.

SUMMARY OF THE INVENTION

It has been the inventors' experience that there are at least three time constants associated with the equivalent circuit of a lithium/iodine battery. Thus, the internal impedance of the battery is time dependent to a significant degree. In order for a measurement of impedance to be of practical value, it would be desirable for the measurement to be related to data collected during qualification testing of the battery. This would allow for a more accurate measurement of impedance and therefore assist in determining remaining battery capacity throughout the battery's life.

Manufacturers of lithium/iodine batteries typically perform qualification tests on each battery in order to verify the suitability of the batteries for use in the highly critical context of implantable medical devices. The data obtained during such qualification testing usually includes two values: the steady-state voltage delivered by the battery across a known impedance; and the internal impedance of the battery. The internal impedance is typically measured by applying a sinusoidal perturbation (usually a sinusoidal current signal) at a frequency of one kilohertz. It is therefore believed to be particularly desirable to implement an EOL indicator circuit which provides information that can be interpreted in direct relation to one of these two quantities.

It has been the inventors' experience that the internal impedance of a battery corresponds closely to the impedance measured at one kilohertz if two specific conditions are met. First, the internal battery impedance must be measured by a change in voltage resulting from a known change in a known load impedance, rather than a single voltage measurement taken across the known load impedance. Second, the change in voltage must be measured in a time window extending from approximately one to ten milliseconds after the change in the load impedance.

Although some impedance measurement circuits in the prior art appear to meet the first condition set forth above, it is believed that the ability to relate measured impedance to electrical data collected during manufacturers' qualification testing has not heretofore been disclosed in the prior art. In accordance with one aspect of the present invention, therefore, there is provided an arrangement whereby such ability to correlate qualification data and EOL data is provided.

In accordance with another aspect of the present invention, there is provided an arrangement whereby reliable information about battery depth-of-discharge can be obtained during the early and middle stages of battery depletion, this information being complementary to the internal impedance data which has primary significance during the later stages of battery depletion. Thus, information about battery depth-of-discharge is available throughout the battery's life.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF THE SPECIFIC EMBODIMENT OF THE INVENTION

Figure 1:
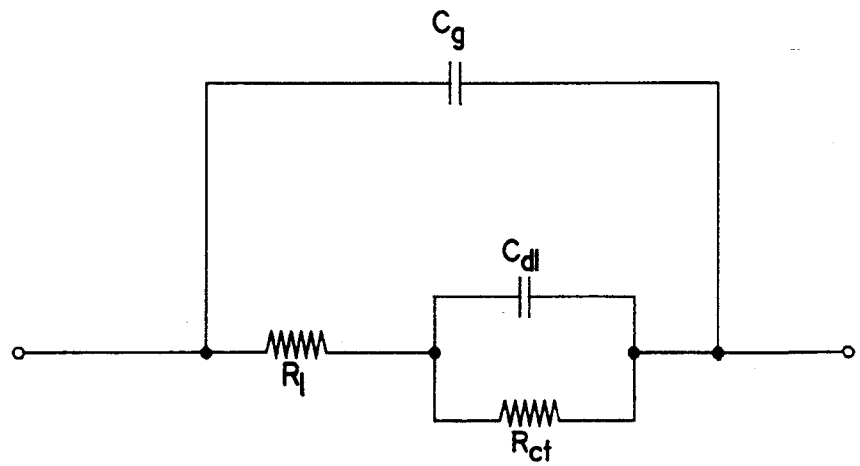
FIG. 1 is a schematic diagram of an equivalent circuit approximation for a lithium-iodine cell.

Referring to FIG. 1, there is shown an equivalent circuit which can be used as a conceptual model of a lithium-iodine battery. By equivalent circuit, it is meant that for the purposes of circuit analysis, the circuit of FIG. 1 can be substituted in place of a lithium-iodine battery in a circuit diagram which includes such a battery. An equivalent circuit is useful for this purpose since in a real application, as opposed to an idealized one, a lithium-iodine battery behaves as more than a simple voltage source. In particular, a lithium-iodine battery possesses its own complex impedance (resistance, capacitance, inductance) characteristics which can have an effect on the operation of the circuit in which it is included. As would be appreciated by those of ordinary skill in the art, the equivalent circuit of FIG. 1 is a simplified approximation of a lithium-iodine battery.

The components in the equivalent circuit of FIG. 1 can be interpreted as follows: $C_g$ is the "geometric capacitance", $R_1$ is the ohmic resistance of the electrolyte and cathode material in the battery, $R_{ct}$ is the composite non-ohmic resistance for the anode and cathode charge-transfer reactions, and $C_{dl}$ is the composite double-layer capacitance for the anode/electrolyte and cathode/electrolyte interfaces. In more fully-developed equivalent circuit representations of lithium-iodine cells, other components may also be included; however, the circuit of FIG. 1 has been found to be sufficiently representative of the behavior of a lithium-iodine cell for the purposes of the present invention. Other refinements that might be made to the equivalent circuit of FIG. 1 are believed to be significant primarily in other contexts not relevant here, such as for the modelling of low-impedance cells at high frequencies.

Using the equivalent circuit of FIG. 1, the inventors have determined that there exists a high degree of correlation between the depth-of-discharge of a lithium-iodine cell and the geometric capacitance $C_g$ of the cell. Preliminary data suggests that this correlation may be due, at least in part, to the decreasing dielectric constant of the composite LiI/liquid electrolyte with increasing depth-of-discharge; however, there are probably several contributing factors, including the decrease in cathode area. The geometric capacitance changes rapidly during the early and mid depth-of-discharge ranges. However, the geometric capacitance also experiences a significant decrease between EOL and complete depletion of the battery. In this sense, the characteristics of the geometric capacitance are complementary to the internal impedance value, which changes little during the early and mid depth-of-discharge ranges and then increases rapidly near EOL.

Figure 2:
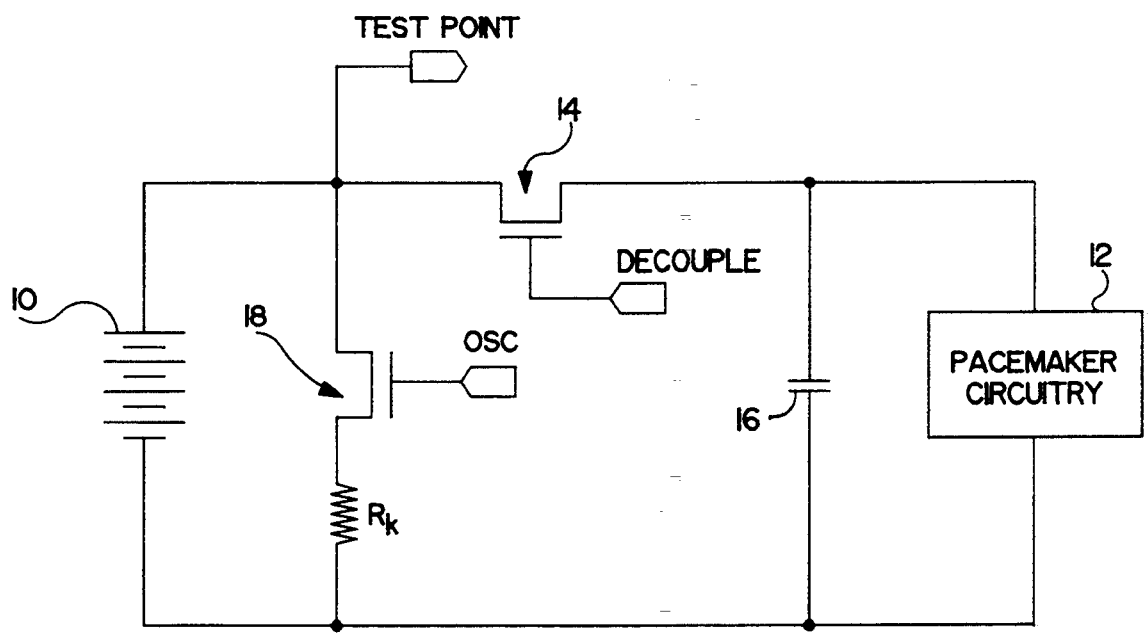
FIG. 2 is a schematic diagram of a depth-of-discharge measurement circuit in accordance with one embodiment of the invention.

Turning now to FIG. 2, there is shown a simplified schematic representation of a circuit which may be employed in an implantable device to measure the internal impedance and the geometric capacitance of a lithium-iodine cell. It is to be understood that the circuit of FIG. 2 is but one possible circuit for performing the measurements in accordance with the present invention. A variety of different circuits have been proposed in the prior art for temporarily decoupling an implantable device's battery from the circuitry of the device and for applying known currents or voltages to the terminals of the decoupled battery in order to obtain readings of, for example, the internal impedance of the battery or the voltage output of the battery. It is believed that any of the known circuits for performing these functions (such as are disclosed in the above-referenced patents) could be readily adapted to the practice of the present invention by those of ordinary skill in the art having the benefit of the present disclosure.

The schematic diagram of FIG. 2 shows a lithium-iodine battery which is coupled to pacemaker circuitry 12 to supply DC power thereto. However, battery 10 is capable of being decoupled from pacemaker circuitry 12 by rendering a transistor 14 non-conductive. As shown in FIG. 2, the gate of transistor 14 receives a DECOUPLE signal, so that when DECOUPLE is deasserted, battery 10 is prevented from supplying DC power to circuitry 12. A capacitor 16 is included in the circuit of FIG. 2 to provide a temporary source of power to circuitry 12 when battery 10 is decoupled therefrom.

When transistor 14 is rendered non-conductive, a known resistive load $R_k$ can be coupled between the terminals of battery 10 by rendering a second transistor 18 conductive. When this is done, the resulting output voltage and/or current may be measured at the TEST POINT terminal shown in FIG. 2.

In accordance with the presently disclosed embodiment of the invention, an oscillating square-wave signal OSC is applied to the gate of transistor 18. This has the effect of periodically coupling and decoupling load $R_k$ across the terminals of battery 10, the periodic rate being determined by the frequency of the oscillating signal. As noted above, the internal impedance of a lithium-iodine battery measured at 1 kHz has been shown to correspond closely to the impedance of the battery measured during an interval from one to ten milliseconds following the change in the load. Thus, a measurement of battery voltage during the appropriate time window during each cycle of the OSC input signal will provide data from which the internal impedance of the battery can be determined.

Figure 3A:
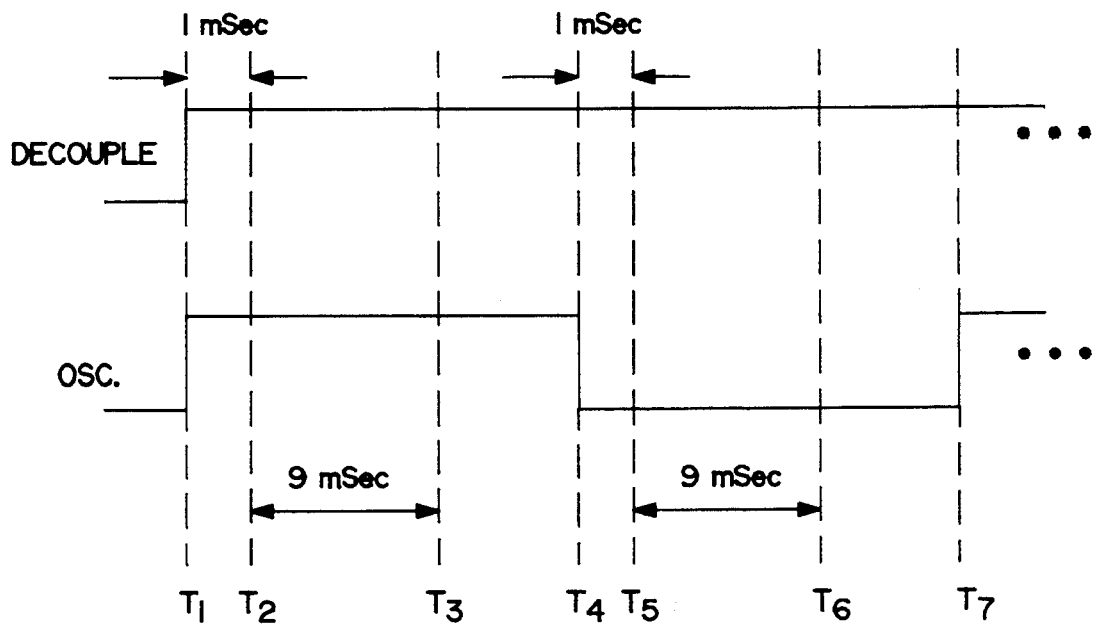
FIGS. 3a and 3b are plots of electrical signals applied to the terminals of the circuit of FIG. 2.

In particular, and with reference now to FIG. 3a, two voltage measurements are made during one period of the oscillating signal, one during each half of the oscillating signal's duty cycle. In FIG. 3a, the signal applied to the DECOUPLE terminal of the circuit of FIG. 2 is designated DECOUPLE, and the signal applied to the OSC terminal of the circuit of FIG. 2 is designated OSC. Beginning at time $T_1$, the DECOUPLE signal is asserted, thereby decoupling battery 10 from pacemaker circuitry 12. At the same time $T_1$, the OSC signal begins the 'on' half of its duty cycle, thereby enabling transistor 18 and effectively coupling load impedance $R_k$ across the terminals of battery 10. During a 9-mSec time window beginning 1-mSec after transistor 18 is first rendered conductive, i.e., during the interval between times $T_2$ and $T_3$ in FIG. 3a, a measurement of the voltage is made at the TEST POINT shown in FIG. 2. This voltage shall be referred to as $V_k$.

At time $T_4$, the OSC signal begins the second, 'off' half of its duty cycle, during which time load impedance $R_k$ is decoupled from the terminals of battery 10. During a 9-mSec window beginning 1-mSec after time $T_4$, a second voltage measurement is taken at the TEST POINT. This voltage shall be referred to as the "open circuit" voltage $V_{oc}$.

At time $T_7$, the OSC signal begins a new cycle. The measurements during the 'on' and 'off' halves of the OSC duty cycle may be repeated in subsequent cycles, in order to verify consistency.

Having obtained at least one $V_k$ and at least one $V_{oc}$ measurement, the internal impedance of the battery $V_{batt}$ can be computed according to Ohm's Law. In particular, a value of the current $I_k$ conducted through the known impedance $R_k$ can be computed according to the following formula:

$$I_k = \frac{V_k}{R_k}$$

Then, the resistance of the battery $V_{batt}$ can be computed according to the following formula:

$$R_{batt} = \frac{\Delta V}{I_k}$$

where $\Delta V$ is given by:

$$\Delta V = (V_{0c} - V_k)$$

From an examination of the foregoing equations, it will be apparent to those of ordinary skill in the art that the circuit of FIG. 2 which allows for the periodic coupling and decoupling of resistor $R_k$ to the terminals of battery 10 provides a means for determining the current drawn from the battery. It is to be understood that various other means for drawing a known current from battery 10, such as current mirror circuits and the like, are known and commonly practiced in the art. It is believed that any such means may be suitable in the practice of the present invention.

It is contemplated that the measured voltage values $V_{oc}$ and $V_k$ may be provided to simple processing circuit included in pacemaker circuitry 12 for computation of the battery impedance $R_{batt}$ within the implanted device. For example, the implanted device may be equipped with a microprocessor adapted to execute a program of instructions for performing the computations in accordance with the foregoing equations. In the alternative, the measured voltage values may be telemetered to an external processing system (for example, in digital form or on a telemetry marker channel) for external computation of battery impedance.

Figure 3B:
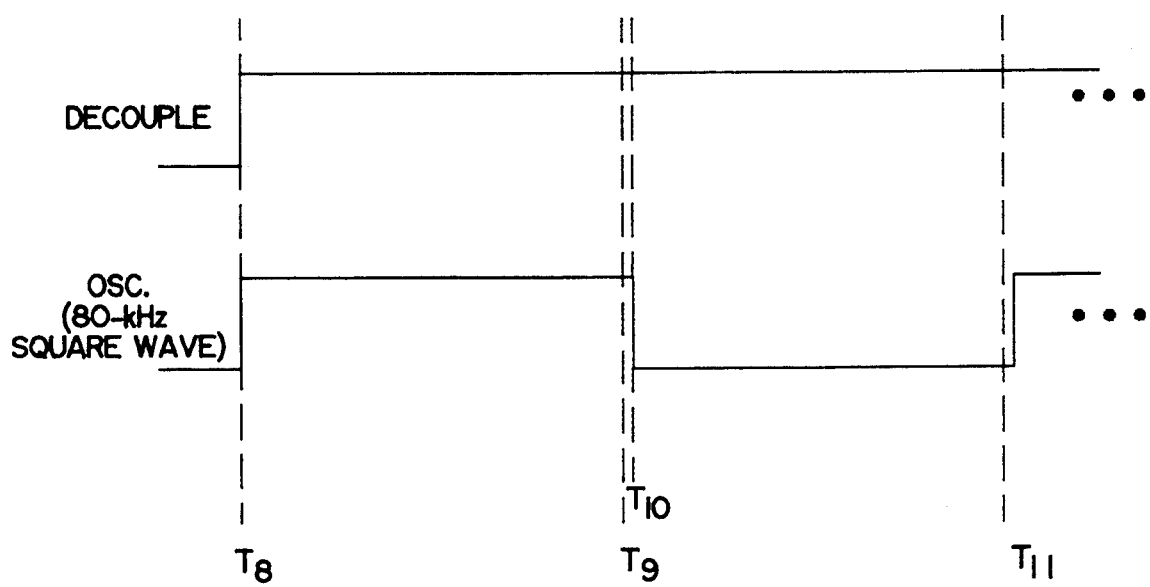

Having obtained a measurement of internal battery impedance, a different oscillating signal, in particular the 80-kHz signal OSC shown in FIG. 3b may be applied to the OSC input in order to measure the geometric capacitance of the battery. In particular, and in accordance with one aspect of the present invention, if an eighty-kilohertz oscillating signal is applied to the OSC input, the resultant voltage differential (i.e., the difference between the battery voltage when transistor 18 is conductive and when it is not conductive) can be measured. With this information, in conjunction with the internal battery impedance measured as previously described, the geometric capacitance of the battery can be determined, as shall be hereinafter describe in greater detail.

With reference to FIG. 3b, geometric capacitance can be measured as follows: At time $T_8$, both the DECOUPLE and 80-kHz OSC signals are asserted, thereby decoupling battery 10 from pacemaker circuitry 12 and applying resistance $R_k$ across the terminals of battery 10. At time $T_8$, shortly before the transition of the OSC signal from the 'on' to the 'off' half of its duty cycle at time $T_{10}$, a measurement of the voltage $V_k$ across $R_k$ is made. Thereafter, at time $T_{10}$, the OSC signal goes low, thereby decoupling resistor $R_k$ from battery 10. At time $T_{11}$, just before the end of the oscillating period of the OSC signal, a measurement of the open-circuit voltage $V_{oc}$ of battery 10 is made.

In accordance with one aspect of the present invention, and as previously discussed, it has been the inventors' experience that the voltage differential $\Delta V = |V_k - V_{oc}|$ when measured at a rate of 80-kHz is closely related to the geometric capacitance $C_g$ of battery 10. The following equation is contemplated to express the particular relationship between the above-noted voltage differential and the geometric capacitance:

$$\ln\left(\frac{V_{oc} - V_{k2}}{V_{oc} - V_{oc2}}\right) = \frac{T}{2 \times R_{batt} C_g}$$

where $V_{oc}$ is the open circuit voltage measured during the above-described determination of $R_{batt}$, $V_{oc2}$ is the open circuit voltage measured during determination of the geometric capacitance, $V_{k2}$ is the voltage across a known load measured during determination of geometric capacitance, and T is the period of the oscillating signal OSC, in this case 12.5-μSec, and where a value of $R_{batt}$ has been previously computed as described hereinabove. Thus, $C_g$ is given by the following formula:

$$C_g = \frac{T}{2 \times R_{batt} \times \ln\left(\frac{V_{oc} - V_{k2}}{V_{oc} - V_{oc2}}\right)}$$

The inventors have compiled experimental data verifying the correspondence between a battery's depth-of-discharge and its geometric capacitance. A summary of typical experimental data is set forth in the following Table 1:

TABLE 1

| BATTERY NUMBER | DEPTH OF DISCHARGE | GEOMETRIC CAPACITANCE |
| --- | --- | --- |
| 1 | 20% | 33,000 pF |
| 2 | 20% | 30,000 pF |
| 3 | 53% | 3,900 pF |
| 4 | 53% | 6,300 pF |
| 5 | 53% | 6,800 pF |
| 6 | 95% | 190 pF |
| 7 | 95% | 210 pF |
| 8 | 95% | 270 pF |
| 9 | 100% | 180 pF |
| 10 | 100% | 190 pF |
| 11 | 100% | 180 pF |
| 12 | 100% | 260 pF |

It is contemplated that data such as appears above in Table 1 could be provided in the pacemaker or programmer circuitry to serve as a basis for estimating depth-of-discharge of a battery based upon computed geometric capacitance. In the alternative, a formula could be derived for expressing the correspondence between geometric capacitance and depth-of-discharge, and either the pacemaker circuitry or the programmer could estimate depth-of-discharge by using such a formula. It is to be understood, of course, that the relationship between depth-of-discharge and geometric capacitance is likely to differ with differing battery sizes and types. However, it is believed that it would be a matter of routine for those of ordinary skill in the art to derive, based upon historical and/or experimental data, an expression of the relationship or correlation between depth-of-discharge and geometric capacitance for a given battery type.

Experimental data appears to indicate that the double-layer capacitance $C_{dl}$ in the equivalent circuit of FIG. 1 does not change signficantly during discharge. This suggests that the nature and effective area of the dominant interface (probably the cathode/electrolyte interface) does not change appreciably during discharge. As shown in Table 1 above, however, the geometric capacitance $C_g$ changes by over two orders of magnitude during cell discharge.

Figure 4A:
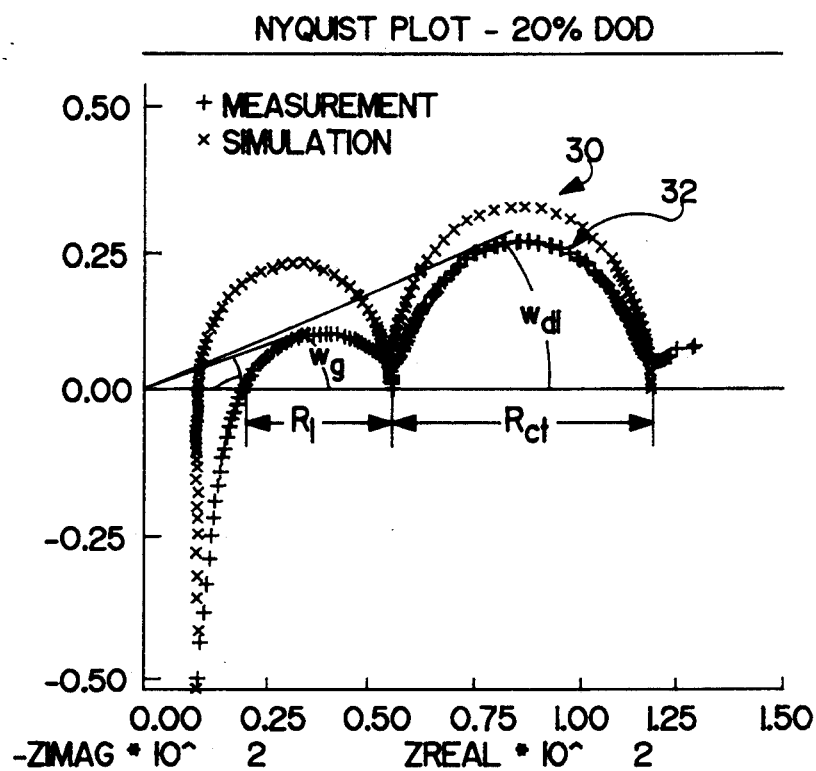
FIGS. 4a, 5a, 6a, and 7a are Nyquist plots of battery impedance over a range of frequencies for batteries at 20%, 53%, 95% and 100% depth-of-discharge, respectively.
Figure 4B:
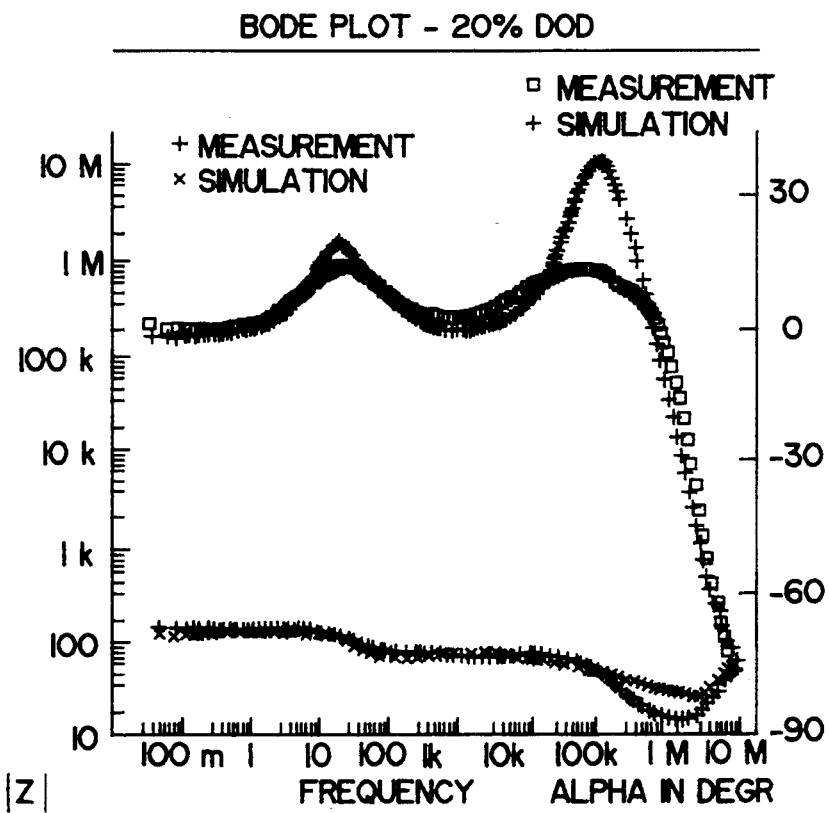
FIGS. 4b, 5b, 6b, and 7b are Bode plots of battery impedance and phase angle over a range of frequencies for batteries at 20%, 53%, 95% and 100% depth-of-discharge, respectively.
Figure 5A:
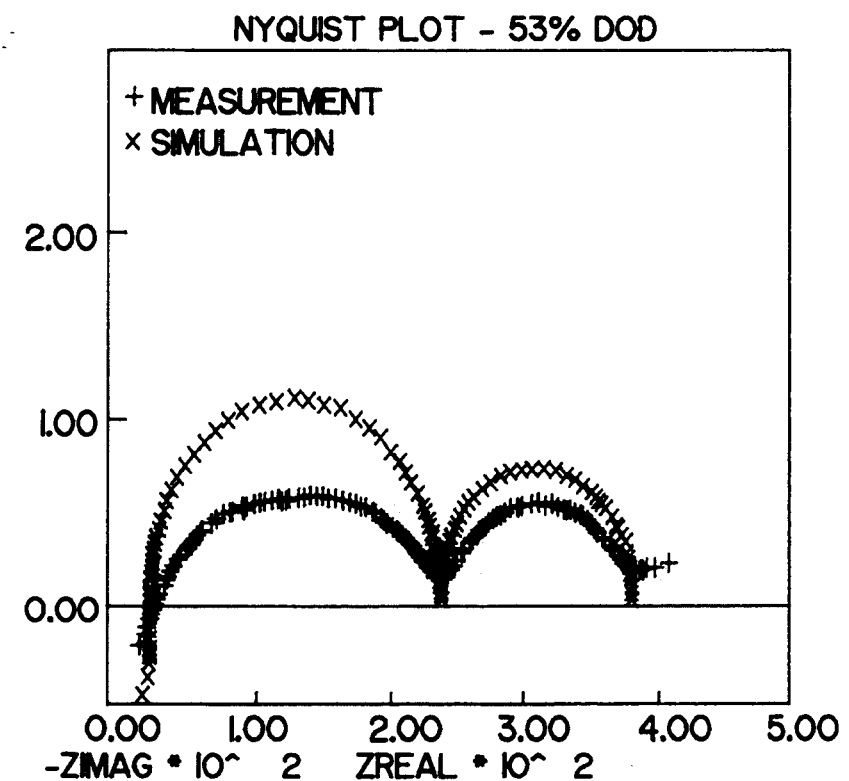
Figure 5B:
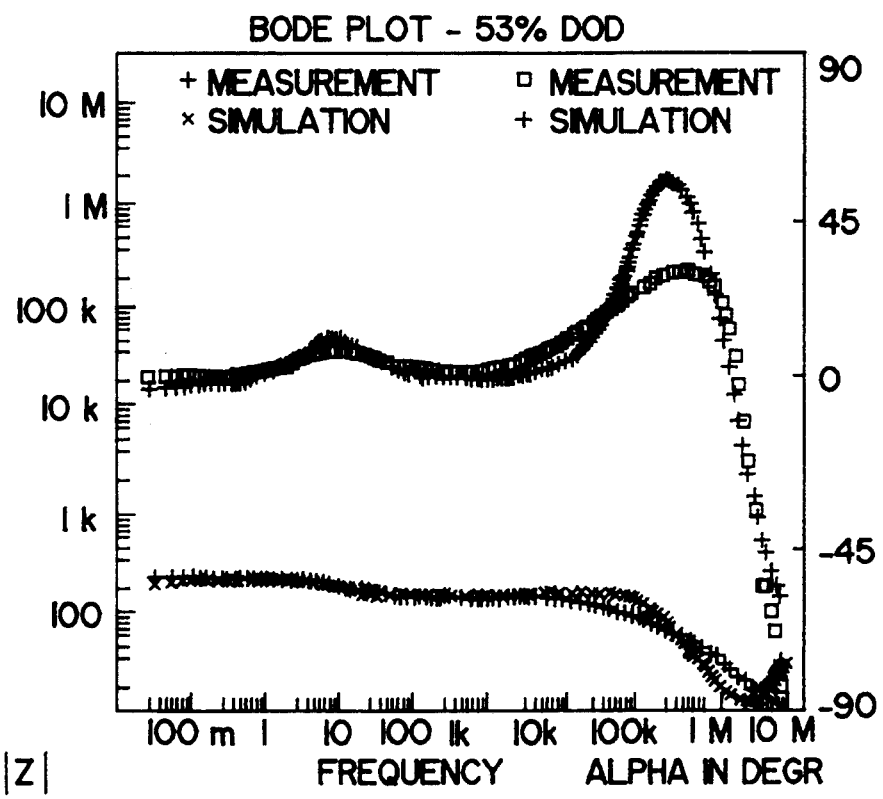
Figure 6A:
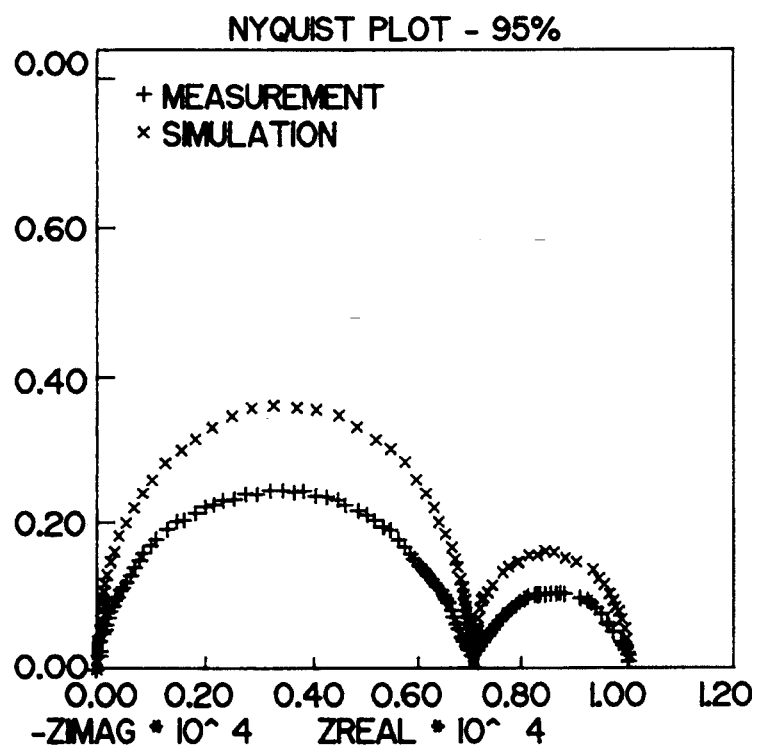
Figure 6B:
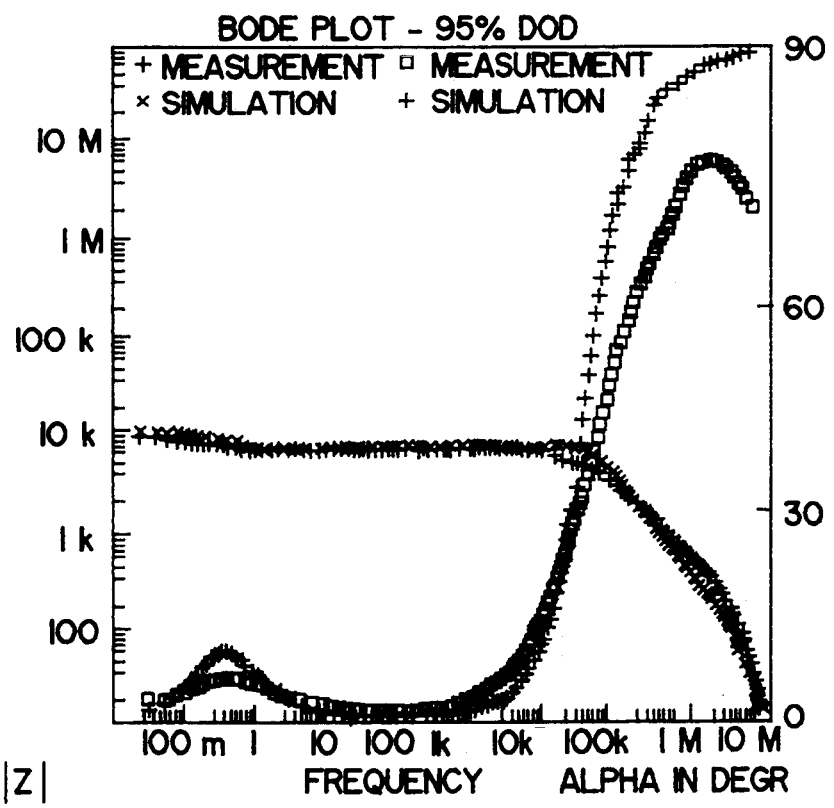
Figure 7A:
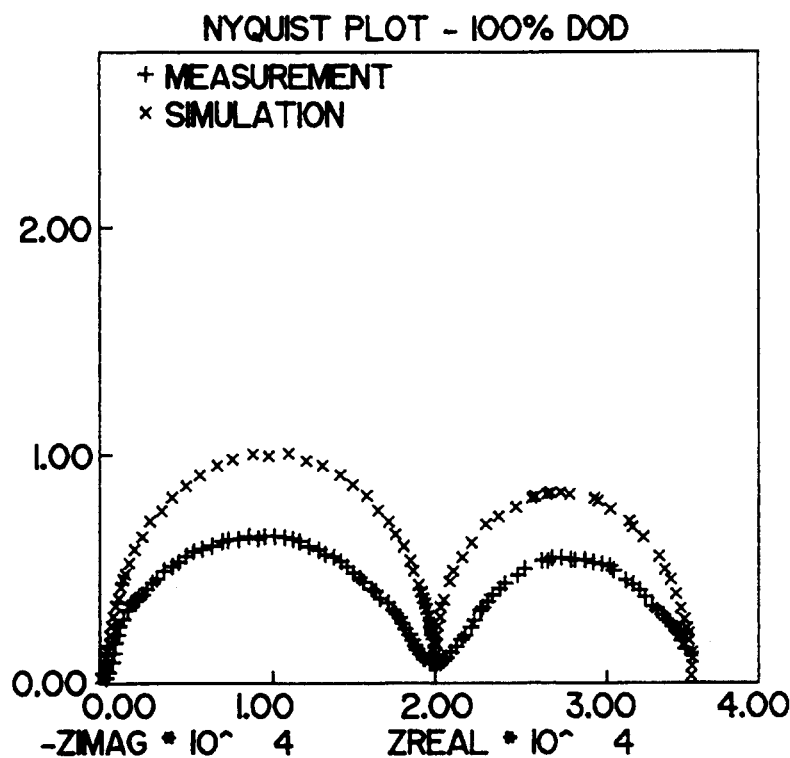
Figure 7B:
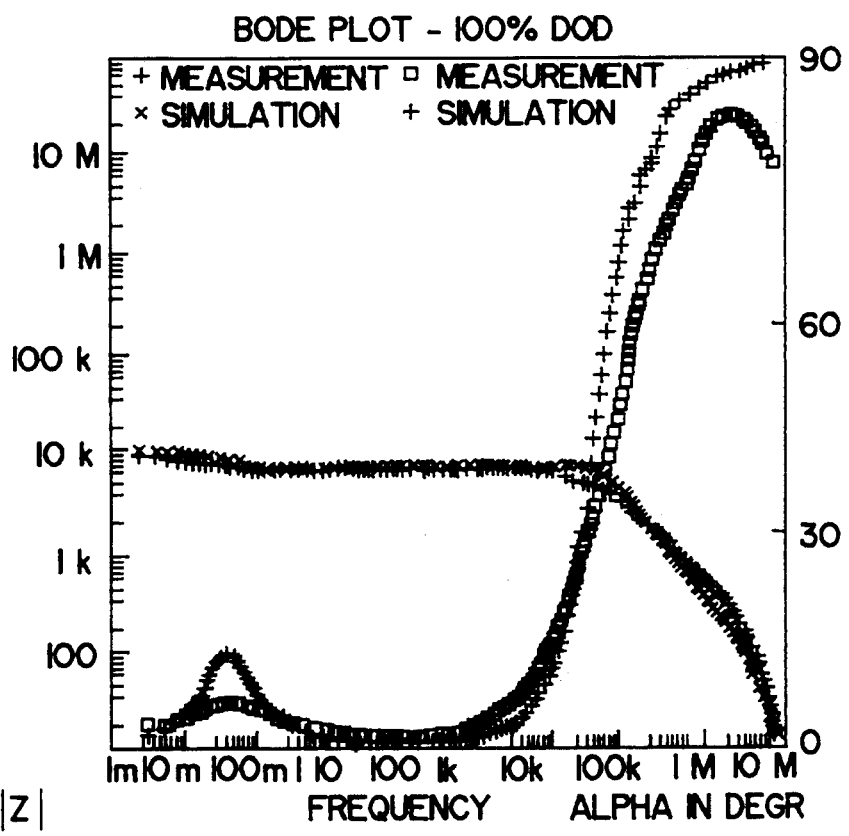

Typical Nyquist and Bode plots for batteries at varying depths-of-discharge are shown in FIGS. 4a–b, 5a–b, 6a–b and 7a–b. Referring to FIG. 4a, there is shown a Nyquist plot of both measured and simulated data for a battery at 20% depth of discharge, the simulated data plot being designated as 30 and the measured data plot being designated as 32. The Nyquist plot of FIG. 4a can be interpreted as follows. First, resistance $R_1$ in the equivalent circuit of FIG. 1 corresponds to the diameter of the left semi-circle on the horizontal (real) axis of the Nyquist plot. Resistance $R_{ct}$ corresponds to the diameter of the right semi-circle on the horizontal (real) axis of FIG. 4a. The double-layer capacitance $C_{dl}$ is given by the following equation:

$$C_{dl} = \frac{1}{\omega_{dl} R_{dl}}$$

where $\omega_{dl}$ is the angular frequency at the apex of the right semi-circle.

Similarly, the geometric capacitance $C_g$ is given by the following equation:

$$C_g = \frac{1}{\omega_g R_1}$$

where $\omega_g$ is the angular frequency at the apex of the left semi-circle.

It should be noted that the impedance behavior of electrochemical systems like lithium-iodine cells is non-ideal and can only be approximated by an equivalent circuit containing only ideal elements. The non-ideal behavior is apparent in the flattened semi-circles observed in the Nyquist plots of FIGS. 4a, 5a, 6a, and 7a. Inspection of the Bode plots of Figs. 4b, 5b, 6b, and 7b shows that the impedance and phase angle produced by the equivalent circuit of FIG. 1 are quite close to the measured data over a broad range of frequencies.

From the foregoing detailed description of specific embodiments of the invention, it should be apparent that a method and apparatus for measuring depth-of-discharge of a lithium-iodine cell in an implantable device has been disclosed. Although specific embodiments of the invention have been described herein in some detail, this has been done for the purposes of illustration only, and should not be taken as limiting with respect to the scope of the invention. It is contemplated that various alterations, substitutions, and modifications may be made to the embodiments described herein without departing from the spirit and scope of the invention as defined in the appended claims which follow.

What is claimed is:

1. A method of measuring depth-of-discharge of a battery delivering a voltage between first and second battery terminals, comprising the steps of measuring said battery's internal impedance and measuring said battery's geometric capacitance, wherein said step of measuring said battery's internal impedance $R_{batt}$ comprises the sub-steps of:

(a) coupling a known impedance $R_k$ between said first and second terminals;
   (b) measuring a voltage $V_k$ between said first and second terminals during a time interval extending from one to ten milliseconds after said step of coupling said known impedance;
   (c) removing said known impedance from said first and second terminals;
   (d) measuring voltage $V_{oc}$ between said first and second terminals during a time interval extending from one to ten milliseconds after said step of removing said known impedance;
   (e) computing said internal impedance according to the formula $$R_{batt} = \frac{R_k(V_{oc} - V_k)}{V_k}$$

and wherein said step of measuring said battery's geometric capacitance comprises the sub-steps of:

(f) alternately coupling and decoupling a known impedance $R_{k2}$ between said first and second battery terminals at a periodic rate T;
   (g) measuring a voltage $V_{oc2}$ between said battery terminals when said known impedance $R_{k2}$ is decoupled from said battery terminals in step (f);
   (h) measuring a voltage $V_{k2}$ between said battery terminals when said known impedance $R_{k2}$ is coupled to said battery terminals in step (f);
   (i) computing said geometric capacitance according to the formula $$\ln\left(\frac{V_{oc} - V_{k2}}{V_{oc} - V_{oc2}}\right) = \frac{T}{2 \times R_{batt} C_g}.$$

2. The method of claim 1, wherein said periodic rate is at least 80-kHz.

3. An apparatus for measuring depth-of-discharge of a lithium-iodine battery in an implantable device, said battery having first and second battery terminals, said apparatus comprising:

(a) a decoupling circuit adapted to temporarily isolate said first and second terminals;
   (b) a loading circuit, coupled between said first and second battery terminals and adapted to alternately couple and decouple a known impedance $R_k$ between said first and second battery terminals at a first periodic rate;
   (c) a voltage measurement circuit, responsive to said loading circuit operating at said first periodic rate to measure a voltage $V_k$ between said first and second battery terminals during a predetermined time interval after said known impedance is coupled between said first and second battery terminals and further adapted to measure a voltage $V_{oc}$ between said first and second battery terminals during a predetermined time interval after said known impedance is decoupled from between said first and second battery terminals;
   (d) a computation circuit, coupled to said voltage measurement circuit and adapted to compute said battery's internal impedance using said $V_k$ and $V_{oc}$ values;
   (e) said loading circuit being further adapted to alternately couple and decouple said known impedance between said first and second terminals at a second periodic rate;
   (f) said voltage measurement circuit further responsive to said loading circuit operating at said second periodic rate to repeatedly and at said second periodic rate, measure voltage between said battery terminals;
   (g) said computation circuit being further adapted to compute said battery's geometric capacitance using said voltage measurements taken at said second periodic rate.

4. The apparatus of claim 3, wherein said second periodic rate is at least 80-kHz.

* * * * *